US012694592B2

(12) United States Patent
Nemoto

(10) Patent No.: US 12,694,592 B2
(45) Date of Patent: Jul. 28, 2026

(54) MEDICAL IMAGE PROCESSING APPARATUS, MEDICAL IMAGE PROCESSING METHOD, AND X-RAY CT APPARATUS

(71) Applicant: Canon Kabushiki Kaisha, Tokyo (JP)

(72) Inventor: Takuya Nemoto, Hitachinaka (JP)

(73) Assignee: Canon Kabushiki Kaisha, Tokyo (JP)

( * ) Notice: Subject to any disclaimer, the term of this patent is extended or adjusted under 35 U.S.C. 154(b) by 106 days.

(21) Appl. No.: 18/792,617

(22) Filed: Aug. 2, 2024

(65) Prior Publication Data

US 2025/0054207 A1 Feb. 13, 2025

(30) Foreign Application Priority Data

Aug. 7, 2023 (JP) ................................. 2023-128351

(51) Int. Cl.
| | |
|---|---|
| *A61B 6/00* | (2024.01) |
| *A61B 6/03* | (2006.01) |
| *A61B 6/06* | (2006.01) |
| *G06T 12/10* | (2026.01) |

(52) U.S. Cl.
CPC .............. *G06T 12/10* (2026.01); *A61B 6/032* (2013.01); *A61B 6/06* (2013.01); *A61B 6/5205* (2013.01); *A61B 6/54* (2013.01); *G06T 2210/41* (2013.01); *G06T 2211/441* (2023.08)

(58) Field of Classification Search
CPC ................. G06T 12/10; G06T 2210/41; G06T 2211/441; A61B 6/032; A61B 6/06; A61B 6/5205; A61B 6/54; A61B 6/481
See application file for complete search history.

(56) References Cited

U.S. PATENT DOCUMENTS

2006/0241402 A1 10/2006 Ichihara et al.
2020/0294288 A1* 9/2020 Smith ..................... G06T 12/30

FOREIGN PATENT DOCUMENTS

JP 2011-156402 A 8/2011

* cited by examiner

*Primary Examiner* — Courtney D Thomas
(74) *Attorney, Agent, or Firm* — Oblon, McClelland, Maier & Neustadt, L.L.P.

(57) ABSTRACT
According to one embodiment, a medical image processing apparatus includes processing circuitry. The processing circuitry acquires first projection data obtained by non-contrast scanning on a first region of a subject, and second projection data obtained by contrast scanning on the first region. The processing circuitry extracts third projection data corresponding to a second region in the first region from the second projection data. The processing circuitry reconstructs a first image based on the first projection data, a second image based on the second projection data, and a third image based on a difference between the first projection data and the third projection data. The processing circuitry derives the second image from the first projection data and the third projection data, using a model trained with training data in which the first image and the third image are input data and the second image is correct answer data.

6 Claims, 10 Drawing Sheets

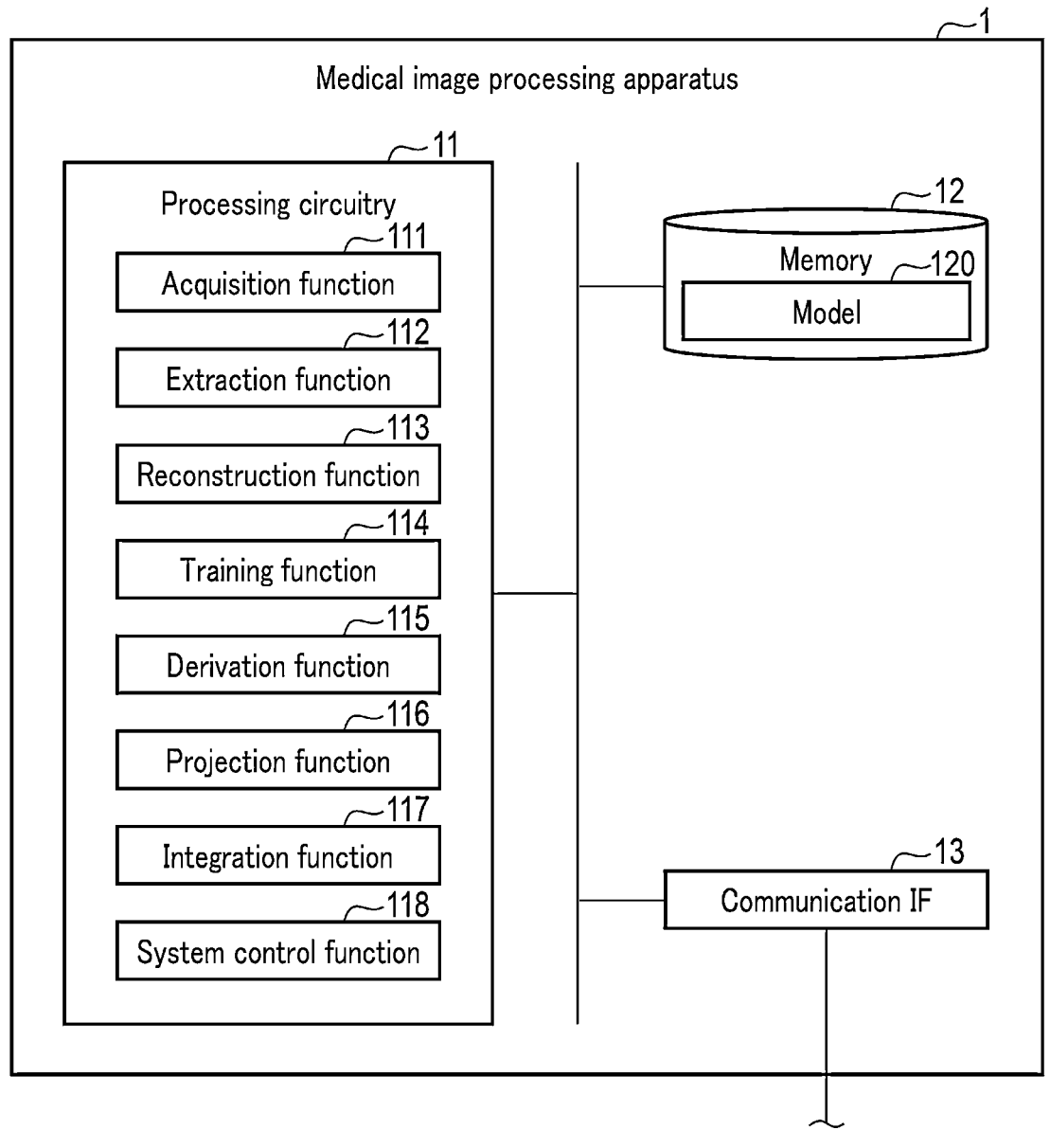
Medical image processing apparatus ~1
Processing circuitry ~11
Acquisition function ~111
Extraction function ~112
Reconstruction function ~113
Training function ~114
Derivation function ~115
Projection function ~116
Integration function ~117
System control function ~118
Memory ~12
Model ~120
Communication IF ~13
F I G. 2

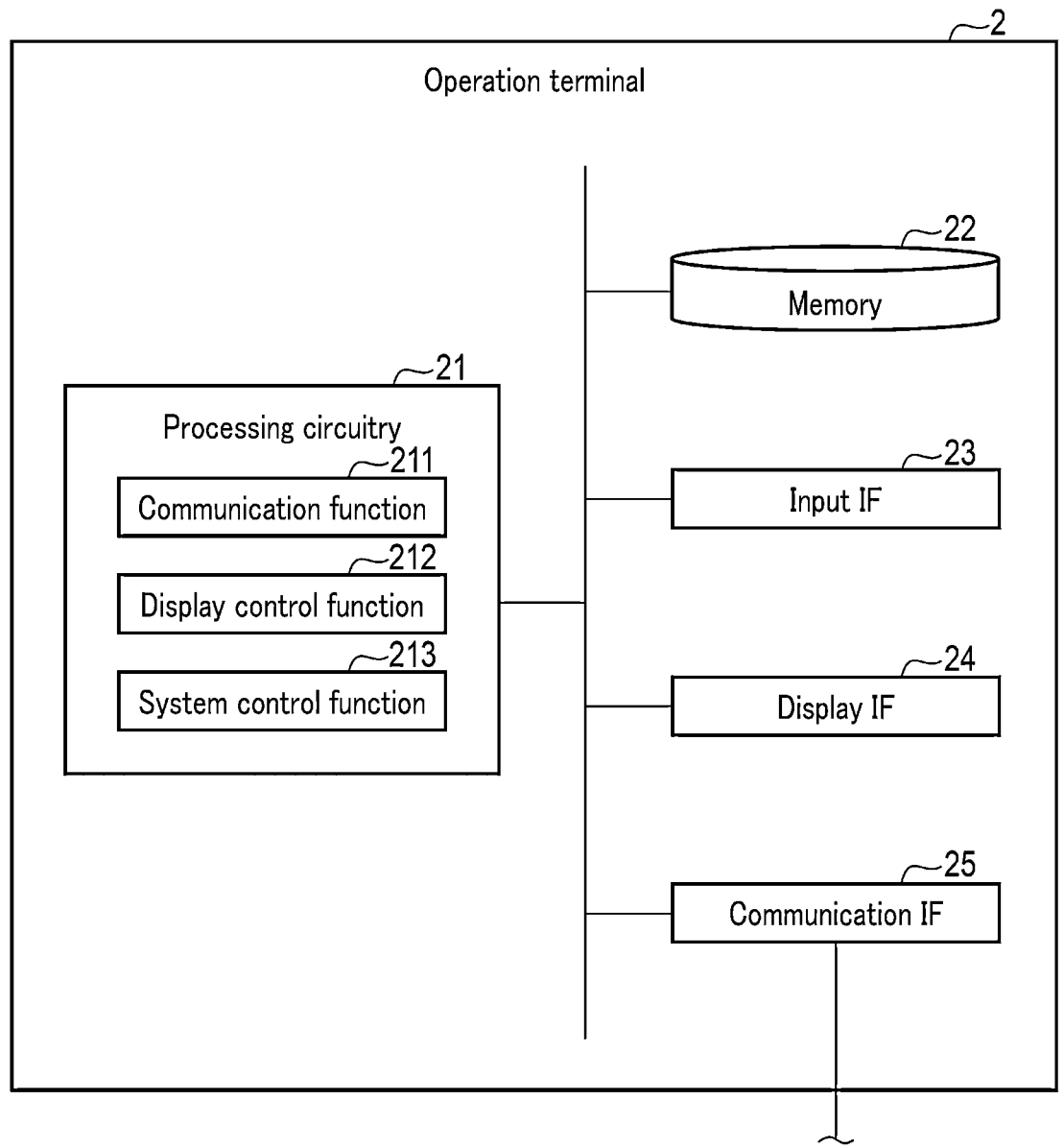
F I G. 3

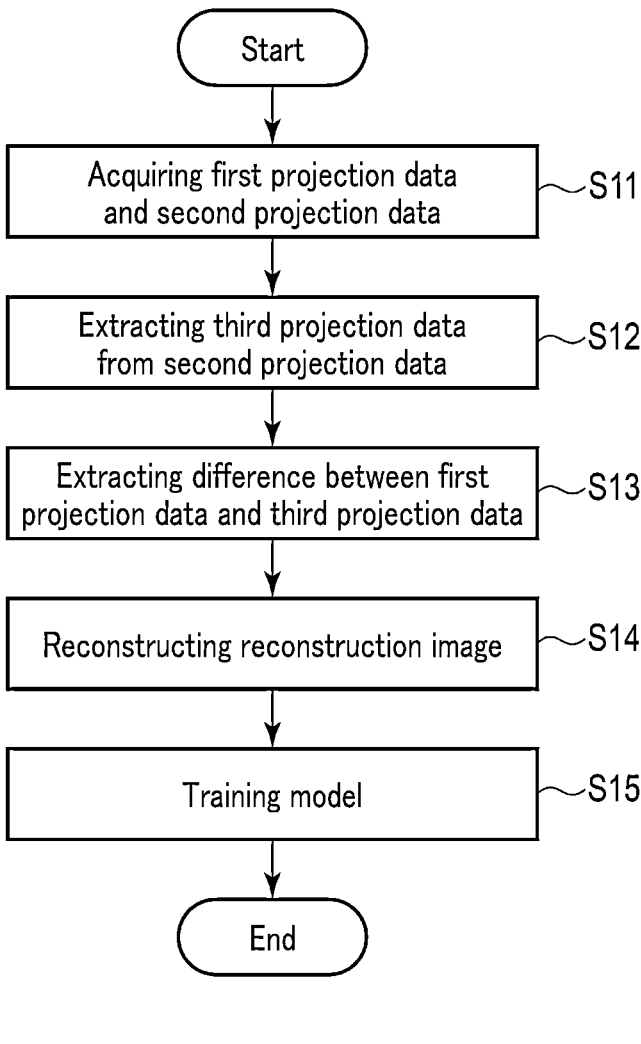
F I G. 4

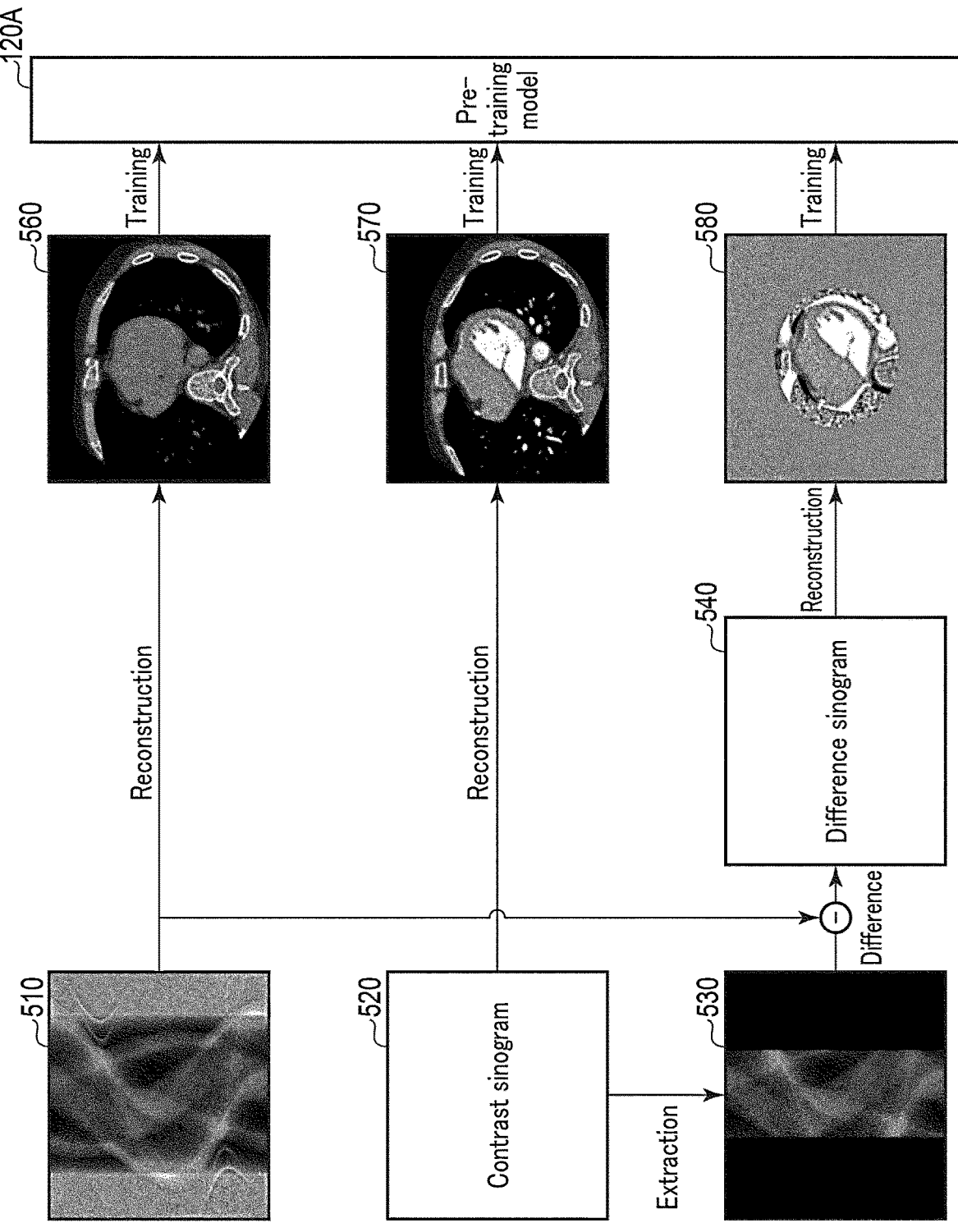
F I G. 5

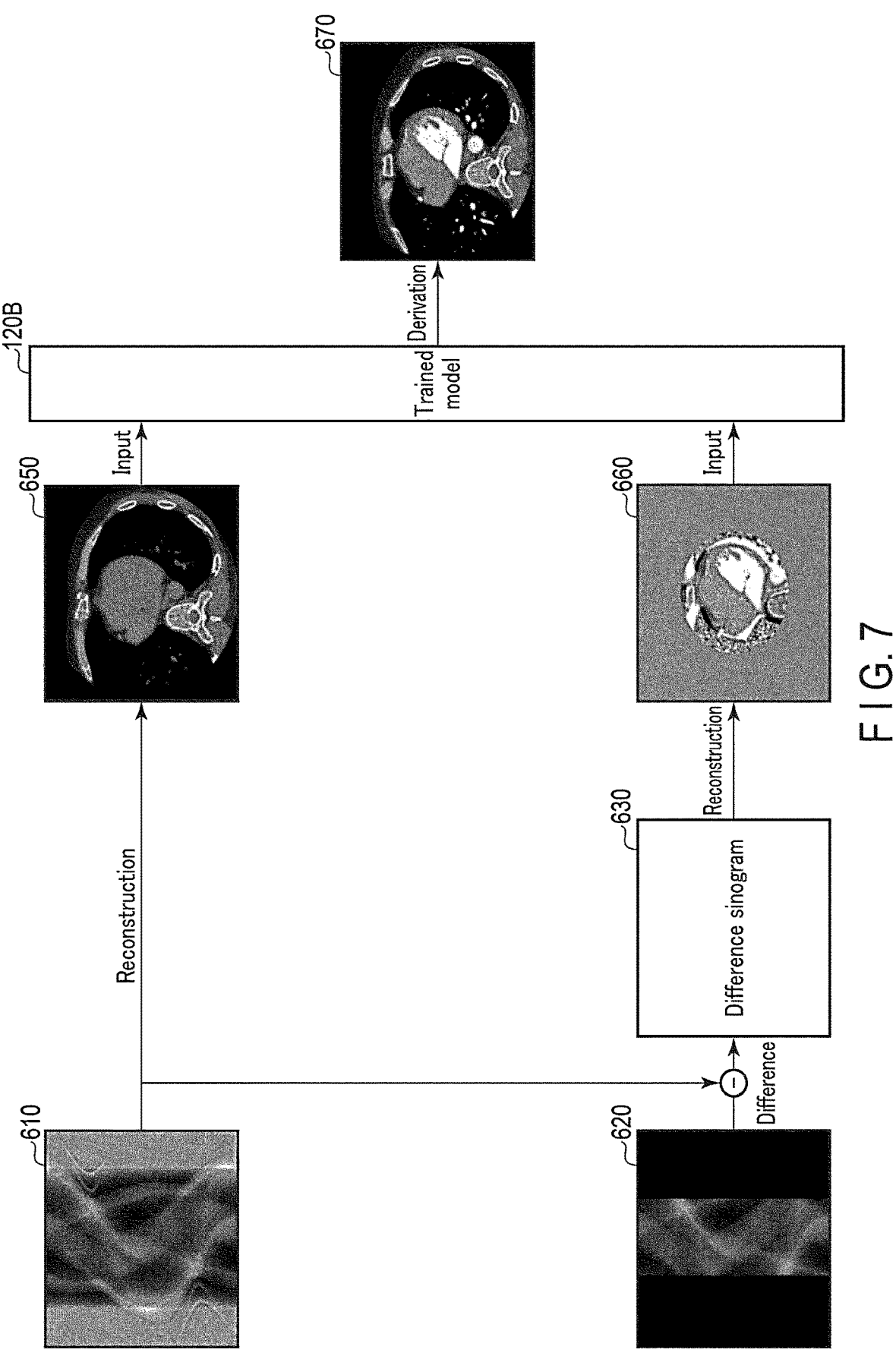
F I G. 7

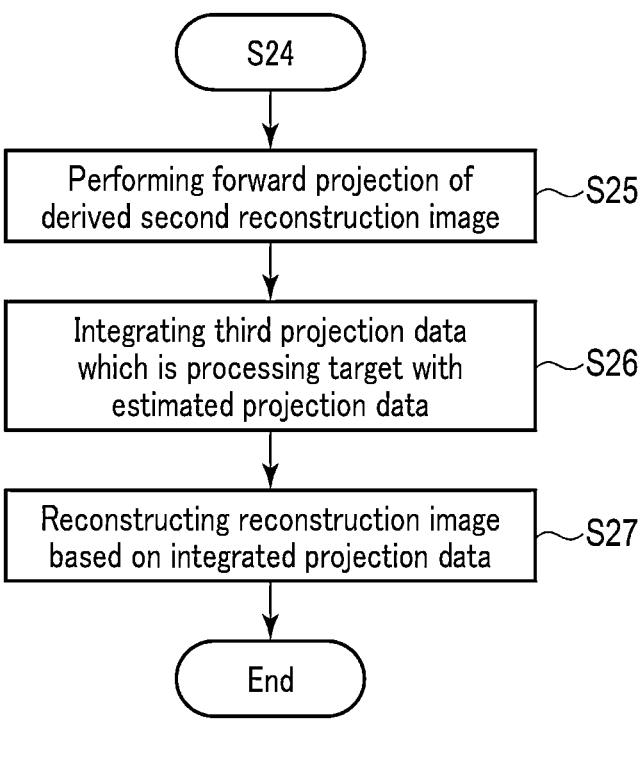
F I G. 8

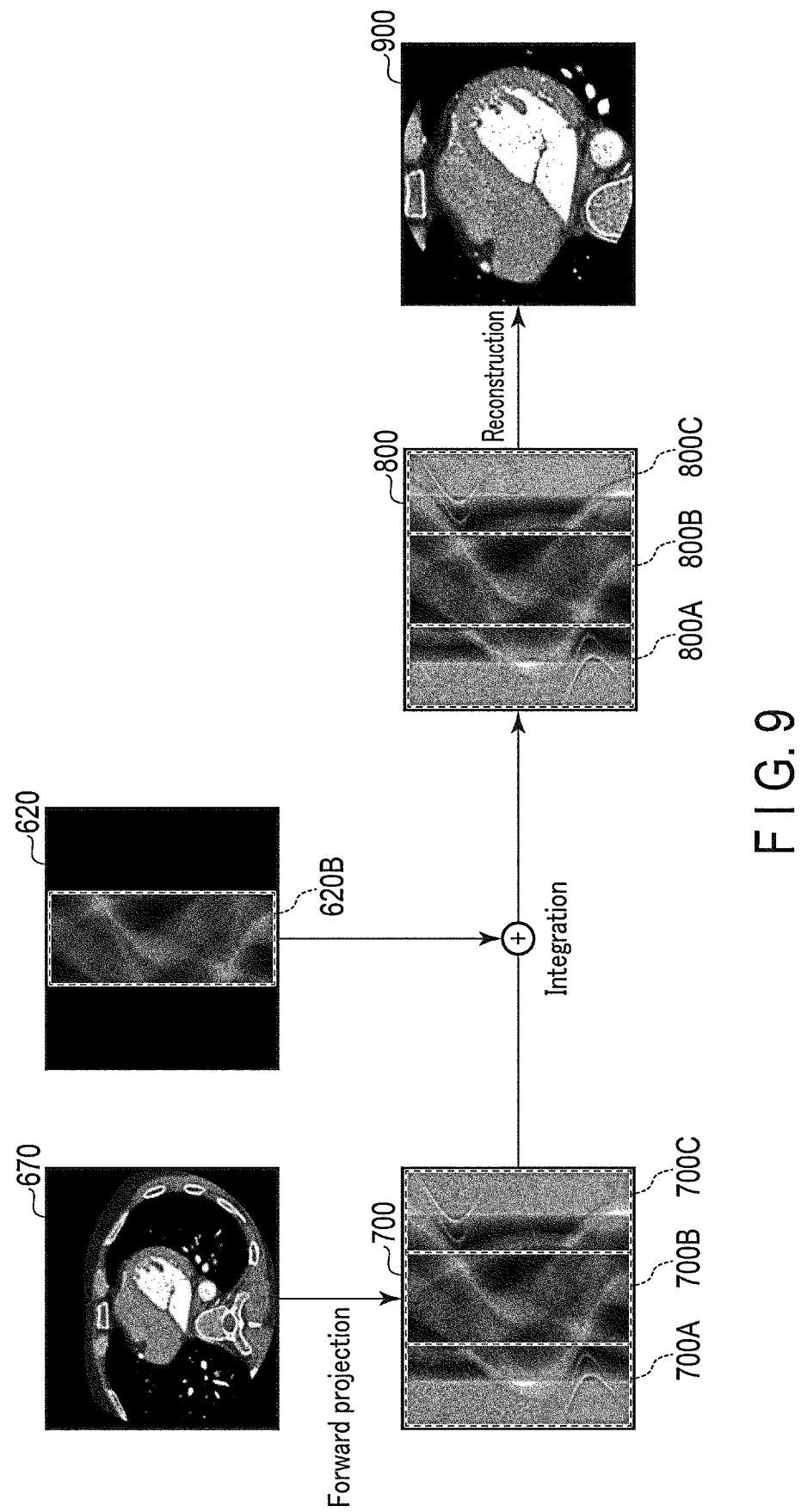
F I G. 9

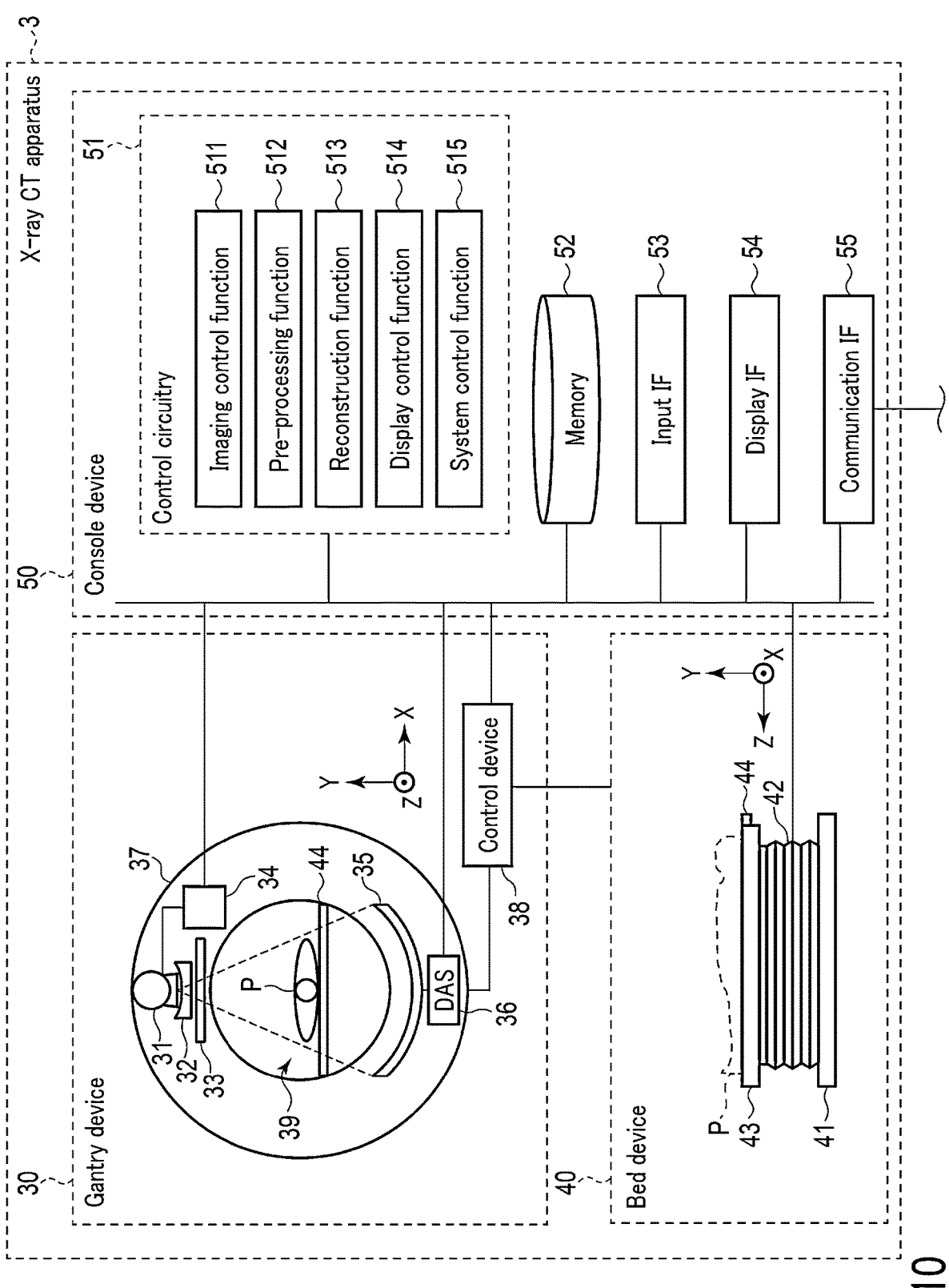
F I G. 10

MEDICAL IMAGE PROCESSING APPARATUS, MEDICAL IMAGE PROCESSING METHOD, AND X-RAY CT APPARATUS

CROSS-REFERENCE TO RELATED APPLICATIONS

This application is based upon and claims the benefit of priority from Japanese Patent Application No. 2023-128351, filed Aug. 7, 2023, the entire contents of which are incorporated herein by reference.

FIELD

Embodiments described herein relate generally to a medical image processing apparatus, a medical image processing method, and an X-ray CT apparatus.

BACKGROUND

An X-ray CT apparatus performs dynamic imaging (perfusion CT imaging) by injecting a contrast agent into a subject in order to evaluate physiological functions related to the heart of the subject. Such an X-ray CT apparatus evaluates the blood flow rate of the myocardium or coronary artery by analyzing a time density curve (TDC) of a contrast agent that has reached the myocardium or coronary artery.

However, the X-ray CT apparatus continuously images the heart over a plurality of heartbeats in dynamic imaging, which increases the exposure dose as compared to normal CT imaging. In order to reduce the exposure dose, methods such as low tube voltage imaging, dual energy imaging, successive approximation reconstruction, and deep learning-based reconstruction have been proposed. In addition to these methods, an imaging or reconstruction method that involves a lower exposure dose is required.

BRIEF DESCRIPTION OF THE DRAWINGS

FIG. 2 is a block diagram showing a configuration example of a medical image processing apparatus according to the first embodiment.

FIG. 3 is a block diagram showing a configuration example of an operation terminal according to the first embodiment.

FIG. 4 is a flowchart showing a training example of a model according to the first embodiment.

FIG. 5 is a schematic diagram showing a training example of a model according to the first embodiment.

FIG. 7 is a schematic diagram showing an application example of a model according to the first embodiment.

FIG. 8 is a flowchart showing a reconstruction example of a reconstruction image according to the first embodiment.

FIG. 9 is a schematic diagram showing a reconstruction example of a reconstruction image according to the first embodiment.

FIG. 10 is a block diagram showing a configuration example of an X-ray CT apparatus according to a second embodiment.

DETAILED DESCRIPTION

In general, according to one embodiment, a medical image processing apparatus includes processing circuitry.

The processing circuitry acquires first projection data obtained by performing non-contrast scanning on a first imaging region of a subject, and second projection data obtained by performing contrast scanning on the first imaging region. The processing circuitry extracts third projection data corresponding to a second imaging region in the first imaging region from the second projection data. The processing circuitry reconstructs a first reconstruction image based on the first projection data, a second reconstruction image based on the second projection data, and a third reconstruction image based on a difference between the first projection data and the third projection data. The processing circuitry derives the second reconstruction image as a processing result from the first projection data and the third projection data as processing targets, using a model trained with training data in which the first reconstruction image and the third reconstruction image are set to input data and the second reconstruction image is set to correct answer data.

Hereinafter, embodiments will be described with reference to the drawings. In the embodiments described below, elements assigned the same reference symbols are assumed to perform the same operations, and redundant descriptions will be suitably omitted.

First Embodiment

Figure 1:
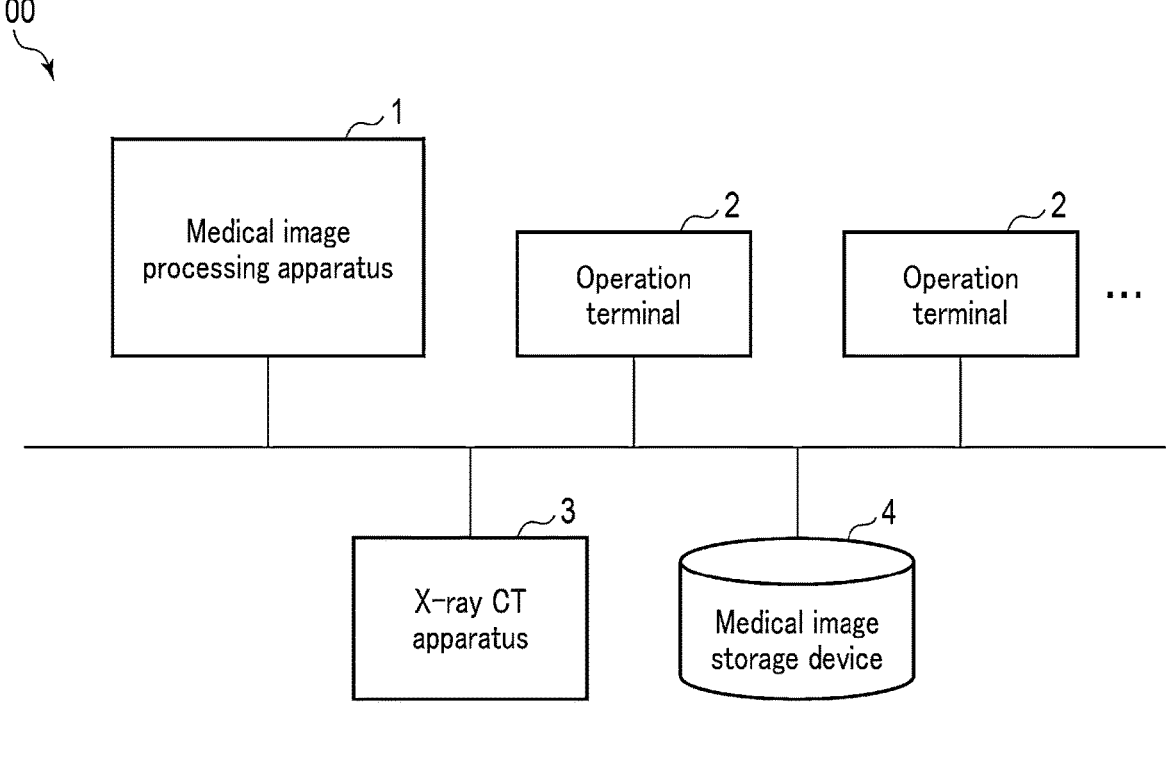
FIG. 1 is a block diagram showing a configuration example of a medical image processing system according to a first embodiment.

FIG. 1 is a block diagram showing a configuration example of a medical image processing system 100 according to a first embodiment. The medical image processing system 100 is a system that processes medical image data, etc., of a subject. The medical image processing system 100 includes, as respective components, a medical image processing apparatus 1, a plurality of operation terminals 2, an X-ray CT apparatus 3, and a medical image storage device 4. The respective components are communicably connected to each other via a bus that is a common signal communication path.

The medical image processing apparatus 1 is a system that processes medical image data, etc., of a subject. The medical image processing apparatus 1 functions as a server of the medical image processing system 100. The medical image processing apparatus 1 may be a workstation that may perform high-speed information processing. The medical image processing apparatus 1 processes data transmitted from the operation terminal 2, the X-ray CT apparatus 3, or the medical image storage device 4, and transmits the processed data to the operation terminal 2, the X-ray CT apparatus 3, or the medical image storage device 4.

The operation terminal 2 is a terminal that is operated by a user. The operation terminal 2 functions as a client of the medical image processing system 100. The operation terminal 2 may be a desktop PC, a notebook PC, a smartphone, a tablet terminal, or a wearable terminal.

The X-ray CT apparatus 3 is a device that generates a sinogram (an example of projection data), CT image data (an example of medical image data), etc., of a subject by performing X-ray CT imaging of the subject. The X-ray CT apparatus 3 transmits the generated data to the medical image storage device 4 (see FIG. 10).

The medical image storage device 4 is a device that stores medical image data, etc. The medical image storage device 4 may be a storage medium (for example, a magnetic storage medium, an electromagnetic storage medium, an optical storage medium, a semiconductor memory), or a drive device that reads and writes data or information to and from the storage medium. The medical image storage device 4 communicates medical image data, etc., with the medical image processing apparatus 1, the operation terminal 2, or the X-ray CT apparatus 3.

FIG. 2 is a block diagram showing a construction example of the medical image processing apparatus 1 according to the first embodiment. The medical image processing apparatus 1 includes, as respective components, processing circuitry 11, a memory 12, and a communication IF 13. The respective components are communicably connected to each other via a bus that is a common signal communication path.

The processing circuitry 11 is circuitry that controls the overall operation of the medical image processing apparatus 1. The processing circuitry 11 includes at least one processor. The processor means, for example, circuitry such as a central processing unit (CPU), a graphics processing unit (GPU), an application-specific integrated circuit (ASIC), a programmable logic device (e.g., a simple programmable logic device (SPLD)), a complex programmable logic device (CPLD), a field programmable gate array (FPGA)), etc. If the processor is a CPU, the CPU realizes respective functions by reading and executing respective programs stored in the memory 12. If the processor is an ASIC, respective functions are directly incorporated as logic circuitry into circuitry of the ASIC. The processor may be configured as single circuitry, or a combination of a plurality of independent circuitry. The processing circuitry 11 realizes respective functions (an acquisition function 111, an extraction function 112, a reconstruction function 113, a training function 114, a derivation function 115, a projection function 116, an integration function 117, a system control function 118).

The acquisition function 111 is a function that acquires various types of data or information. For example, the acquisition function 111 acquires first projection data P1 obtained by performing non-contrast scanning on a first imaging region A1 of a subject, and second projection data P2 obtained by performing contrast scanning on the first imaging region A1. The acquisition function 111 may acquire the first projection data P1 and third projection data P3 that are processing targets. The acquisition function 111 is an example of an acquisition unit.

The extraction function 112 is a function that extracts various types of data or information. For example, the extraction function 112 extracts the third projection data P3 corresponding to a second imaging region A2 in the first imaging region A1 from the second projection data P2. The extraction function 112 may extract a difference between the first projection data P1 and the third projection data P3. The extraction function 112 is an example of an extraction unit.

The reconstruction function 113 is a function that reconstructs various types of data or information. For example, the reconstruction function 113 reconstructs a first reconstruction image R1 based on the first projection data P1, a second reconstruction image R2 based on the second projection data P2, and a third reconstruction image R3 based on a difference between the first projection data P1 and the third projection data P3. The reconstruction function 113 may reconstruct a fourth reconstruction image R4 corresponding to the second imaging region A2 based on the integrated projection data GP. The reconstruction function 113 is an example of a reconstruction unit.

The training function 114 is a function that trains various types of models. For example, the training function 114 trains a model using training data T in which a first reconstruction image R1 and a third reconstruction image R3 are set to input data and a second reconstruction image R2 is set to correct answer data. The training function 114 is an example of a training unit.

The derivation function 115 is a function that derives various types of data or information. For example, the derivation function 115 derives the second reconstruction image R2 that is a processing result from the first projection data P1 and the third projection data P3 that are processing targets, by using a model trained with training data T. The derivation function 115 is an example of a derivation unit.

The projection function 116 is a function that performs various types of projection processing. For example, the projection function 116 obtains estimated projection data EP by performing forward projection of the second reconstruction images R2 derived by the derivation function 115. The projection function 116 is an example of a projection unit.

The integration function 117 is a function that performs various types of integration processing. For example, the integration function 117 obtains integrated projection data GP by integrating the third projection data P3 serving as a processing target with the estimated projection data EP. The integration function 117 is an example of an integration unit.

The system control function 118 is a function of controlling various operations performed by the processing circuitry 11. For example, the system control function 118 provides an operation system (OS) for the processing circuitry 11 to realize respective functions (the acquisition function 111, the extraction function 112, the reconstruction function 113, the training function 114, the derivation function 115, the projection function 116, and the integration function 117). The system control function 118 is an example of a system control unit.

The memory 12 is a device that stores various types of data or information. The memory 12 has a similar hardware configuration to that of the medical image storage device 4. The memory 12 stores respective programs that cause the processing circuitry 11 to realize respective functions (the acquisition function 111, the extraction function 112, the reconstruction function 113, the training function 114, the derivation function 115, the projection function 116, the integration function 117, and the system control function 118). The memory 12 stores a model 120. The memory 12 is an example of a storage unit.

The model 120 is a variety of algorithms. The model 120 may be a machine learning model (e.g., regression, decision tree, random forest, support vector machine, naive Bayes, neural network). In particular, the model 120 may be a deep convolutional neural network (DCNN).

The communication IF 13 is an interface for communicating various types of data or information. For example, the communication IF 13 communicates various types of data or information with the operation terminal 2, the X-ray CT apparatus 3, or the medical image storage device 4. The communication IF 13 is an example of a communication unit.

FIG. 3 is a block diagram showing a construction example of the operation terminal 2 according to the first embodiment. The operation terminal 2 includes processing circuitry 21, a memory 22, an input IF 23, a display IF 24, and a communication IF 25. The respective components are communicably connected to each other via a bus that is a common signal communication path.

The processing circuitry 21 is circuitry that controls the overall operation of the operation terminal 2. The processing circuitry 21 of the operation terminal 2 has a similar hardware configuration to that of the processing circuitry 11 of the medical image processing apparatus 1. The processing circuitry 21 realizes respective functions (a communication function 211, a display control function 212, and a system control function 213).

The communication function 211 is a function for communicating various types of data or information. For example, the communication function 211 communicates various types of data or information with the medical image processing apparatus 1, the X-ray CT apparatus 3, or the medical image storage device 4. The communication function 211 is an example of a communication unit.

The display control function 212 is a function that displays various types of data or information. For example, the display control function 212 causes the display IF 24 to display thereon various types of data or information obtained by the communication function 211. The display control function 212 is an example of a display control unit.

The system control function 213 is a function that controls various types of operations performed by the processing circuitry 21. For example, the system control function 213 provides an operating system (OS) for the processing circuitry 21 to realize respective functions (the communication function 211 and the display control function 212). The system control function 213 is an example of a system control unit.

The memory 22 is a device that stores various types of data or information. The memory 22 of the operation terminal 2 has a similar hardware configuration to that of the memory 12 of the medical image processing apparatus 1. The memory 22 stores respective programs that cause the processing circuitry 21 to realize respective functions (the communication function 211, the display control function 212, and the system control function 213). The memory 22 is an example of a storage unit.

The input IF 23 is an interface that accepts various input operations from a user. The input IF 23 converts various input operations received from the user into electrical signals, and transmits the electrical signals to the processing circuitry 21. The input IF 23 may be a mouse, a keyboard, a button, a panel switch, a slider switch, a trackball, an operation panel, or a touch panel. The input IF 23 is an example of an input unit.

The display IF 24 is an interface that displays various types of data or information. The display IF 24 may be a liquid crystal display, a plasma display, an organic EL display, or an LED display. The display IF 24 may be a touch panel display that also functions as the input IF 23. The display IF 24 is an example of a display unit.

The communication IF 25 is an interface for communicating various types of data or information. For example, the communication IF 25 communicates various types of data or information with the medical image processing apparatus 1, the X-ray CT apparatus 3, or the medical image storage device 4. The communication IF 25 is an example of a communication unit.

FIG. 4 is a flowchart showing a training example of the model 120 according to the first embodiment. According to this example, the medical image processing apparatus 1 trains the model 120 based on the first projection data P1 and the second projection data P2.

(Step S11) First, the medical image processing apparatus 1 uses the acquisition function 111 to acquire the first projection data P1 and the second projection data P2. Specifically, the acquisition function 111 acquires the first projection data P1 and the second projection data P2 from the medical image storage device 4 by gaining access to the medical image storage device 4.

(Step S12) Next, the medical image processing apparatus 1 uses the extraction function 112 to extract the third projection data P3 from the second projection data P2. Specifically, the extraction function 112 extracts the third projection data P3, which is a part of the second projection data P2, from the second projection data P2 acquired in step S11.

(Step S13) Subsequently, the medical image processing apparatus 1 uses the extraction function 112 to extract a difference between the first projection data P1 and the third projection data P3. Specifically, the extraction function 112 extracts the difference between the first projection data P1 acquired in step S11 and the third projection data P3 extracted in step S12.

(Step S14) Subsequently, the medical image processing apparatus 1 uses the reconstruction function 113 to reconstruct a reconstruction image. First, the reconstruction function 113 reconstructs a first reconstruction image R1 based on the first projection data P1 acquired in step S11. Second, the reconstruction function 113 reconstructs a second reconstruction image R2 based on the second projection data P2 acquired in step S11. Third, the reconstruction function 113 reconstructs a third reconstruction image R3 based on the difference extracted in step S13.

(Step S15) Finally, the medical image processing apparatus 1 trains the model 120 using the training function 114. Specifically, the training function 114 generates the training data T in which the first reconstruction image R1 and the third reconstruction image R3 reconstructed in step S14 are set to input data, and the second reconstruction image R2 reconstructed in step S14 is set to correct answer data. The training function 114 trains the model 120 using the generated training data T. After step S15, the medical image processing apparatus 1 terminates a series of operations.

The medical image processing apparatus 1 may repeatedly train the model 120 using a plurality of training data sets. That is, the medical image processing apparatus 1 may sequentially generate training data sets including the first projection data P1 and the second projection data P2, and repeatedly train the model 120 using each of the generated training data sets. This optimizes parameters of the model 120.

FIG. 5 is a schematic diagram showing a training example of the model 120 according to the first embodiment. According to this example, the medical image processing apparatus 1 generates a pre-training model 120A based on a non-contrast sinogram 510 (an example of the first projection data P1) and a contrast sinogram 520 (an example of the second projection data P2). The pre-training model 120A is the model 120 before being trained.

First, the medical image processing apparatus 1 uses the acquisition function 111 to acquire the non-contrast sinogram 510 and the contrast sinogram 520. Specifically, the acquisition function 111 acquires the non-contrast sinogram 510 and the contrast sinogram 520 from the medical image storage device 4 by gaining access to the medical image storage device 4 (see step S11).

The non-contrast sinogram 510 is projection data obtained by a method (non-contrast scanning) of imaging the first imaging region A1 of a subject without injecting a contrast agent into the subject. The non-contrast sinogram 510 is obtained by the X-ray CT apparatus 3 performing simple scanning for calcium score measurement on a body axial section including the subject's heart.

The contrast sinogram 520 is projection data obtained by a method (contrast scanning) of photographing the first imaging region A1 of a subject by injecting a contrast agent into the subject. The contrast sinogram 520 is obtained by the X-ray CT apparatus 3 performing dynamic imaging for time-density curve measurement on a body axial section including the subject's heart.

Next, the medical image processing apparatus 1 uses the extraction function 112 to extract a contrast sinogram 530 (an example of the third projection data P3) from the contrast sinogram 520. Specifically, the extraction function 112 extracts the contrast sinogram 530 related to the second imaging region A2, which is a part of the first imaging region A1, from the contrast sinogram 520 related to the first imaging region A1 (see step S12).

It can be said that the contrast sinogram 530 is projection data obtained by a method (contrast scanning) of photographing the second imaging region A2 of a subject by injecting a contrast agent into the subject. Alternatively, it can be said that the contrast sinogram 530 is projection data obtained by the X-ray CT apparatus 3 performing dynamic imaging for time-density curve measurement on the subject's heart. It can also be said that the contrast sinogram 530 is projection data obtained by truncating the contrast sinogram 520 in a channel direction (lateral direction).

Subsequently, the medical image processing apparatus 1 uses the extraction function 112 to extract a difference between the non-contrast sinogram 510 and the contrast sinogram 530. Specifically, the extraction function 112 extracts a difference sinogram 540 by extracting a difference between a data region of the non-contrast sinogram 510 and a data region of the contrast sinogram 530 (see step S13).

It can be said that the difference sinogram 540 is projection data that shows a portion of the second imaging region A2 of the subject, emphasized by the contrast agent. Alternatively, it can be said that the difference sinogram 540 is projection data in which a contrast effect of the subject's heart is emphasized.

Subsequently, the medical image processing apparatus 1 uses the reconstruction function 113 to reconstruct a non-contrast image 560, a contrast image 570, and a difference image 580. First, the reconstruction function 113 reconstructs the non-contrast image 560 (an example of the first reconstruction image R1) based on the non-contrast sinogram 510. Second, the reconstruction function 113 reconstructs the contrast image 570 (an example of the second reconstruction image R2) based on the contrast sinogram 520. Third, the reconstruction function 113 reconstructs the difference image 580 (an example of the third reconstruction image R3) based on the difference sinogram 540 (see step S14).

Finally, the medical image processing apparatus 1 uses the training function 114 to train the pre-training model 120A. Specifically, the training function 114 generates the training data T in which the non-contrast image 560 and the difference image 580 are set to input data, and the contrast image 570 is set to correct answer data. The training function 114 trains the pre-training model 120A in a framework of supervised learning using the generated training data T (see step S15).

Figure 6:
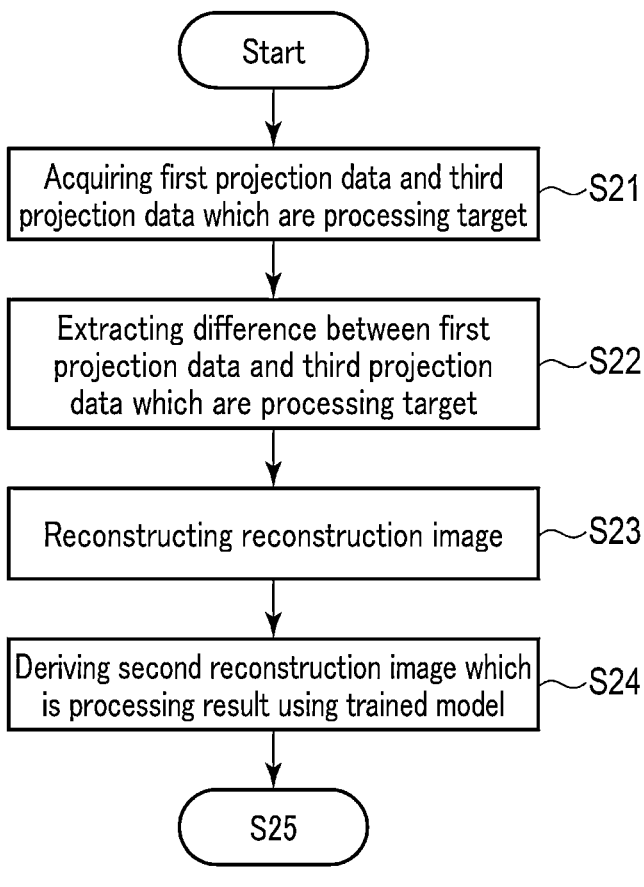
FIG. 6 is a flowchart showing an application example of a model according to the first embodiment.

FIG. 6 is a flowchart showing an application example of the model 120 according to the first embodiment. According to this example, the medical image processing apparatus 1 derives the second reconstruction image R2 that is a processing result, based on the first projection data P1 and the third projection data P3 that are processing targets.

(Step S21) First, the medical image processing apparatus 1 uses the acquisition function 111 to acquire the first projection data P1 and the third projection data P3 that are processing targets. Specifically, the acquisition function 111 gains access to the X-ray CT apparatus 3, thereby acquiring the first projection data P1 and third projection data P3 that are processing targets from the X-ray CT apparatus 3.

(Step S22) Next, the medical image processing apparatus 1 uses the extraction function 112 to extract a difference between the first projection data P1 and the third projection data P3 which are processing targets. Specifically, the extraction function 112 extracts the difference between the first projection data P1 and the third projection data P3 acquired in step S21.

(Step S23) Subsequently, the medical image processing apparatus 1 uses the reconstruction function 113 to reconstruct a reconstruction image. First, the reconstruction function 113 reconstructs the first reconstruction image R1 based on the first projection data P1 that is a processing target and is acquired in step S21. Second, the reconstruction function 113 reconstructs the third reconstruction image R3 based on the difference extracted in step S22.

(Step S24) Subsequently, the medical image processing apparatus 1 uses the derivation function 115 to derive the second reconstruction image R2 that is a processing result, using the trained model 120. Specifically, the derivation function 115 derives, using the model 120 trained in step S15, the second reconstruction image R2 that is a processing result, from the first reconstruction image R1 and the third reconstruction image R3 that are reconstructed in step S23. After step S24, the processing proceeds to step S25 (see FIG. 8).

FIG. 7 is a schematic diagram showing an application example of the model 120 according to the first embodiment. According to this example, the medical image processing apparatus 1 derives a contrast image 670 (an example of the second reconstruction image R2) which is a processing result, based on a non-contrast sinogram 610 (an example of the first projection data P1) and a contrast sinogram 620 (an example of the third projection data P3) which are processing targets, and a trained model 120B. The trained model 120B is the model 120 after being trained.

First, the medical image processing apparatus 1 uses the acquisition function 111 to acquire the non-contrast sinogram 610 and the contrast sinogram 620. Specifically, the acquisition function 111 acquires the non-contrast sinogram 610 and the contrast sinogram 620 from the X-ray CT apparatus 3 by gaining access to the X-ray CT apparatus 3 (see step S21).

The non-contrast sinogram 610 is projection data obtained by a method (non-contrast scanning) of imaging the first imaging region A1 of a subject without injecting a contrast agent into the subject. That is, the non-contrast sinogram 610 is similar to the non-contrast sinogram 510.

The contrast sinogram 620 is projection data obtained by a method (contrast scanning) of photographing the second imaging region A2 of a subject by injecting a contrast agent into the subject. The contrast sinogram 620 is obtained by the X-ray CT apparatus 3 performing dynamic imaging for time-density curve measurement on the subject's heart. A difference is that the contrast sinograms 620 and 530 are projection data related to the second imaging region A2 whereas the contrast sinogram 520 is projection data related to the first imaging region A1.

Next, the medical image processing apparatus 1 uses extraction function 112 to extract a difference between the non-contrast sinogram 610 and the contrast sinogram 620. Specifically, the extraction function 112 extracts a difference sinogram 630 by extracting a difference between a data region of the non-contrast sinogram 610 and a data region of the contrast sinogram 620 (see step S22).

It can be said that the difference sinogram 630 is projection data that shows a portion of the second imaging region A2 of the subject, emphasized by the contrast agent. That is, the difference sinogram 630 is similar to the difference sinogram 540.

Subsequently, the medical image processing apparatus 1 uses the reconstruction function 113 to reconstruct the non-contrast image 650 and the difference image 660. First, the reconstruction function 113 reconstructs the non-contrast image 650 (an example of the first reconstruction image R1) based on the non-contrast sinogram 610. Second, the reconstruction function 113 reconstructs the difference image 660 (an example of the third reconstruction image R3) based on the difference sinogram 630 (see step S23).

Subsequently, the medical image processing apparatus 1 uses the derivation function 115 to derive the contrast image 670 (an example of the second reconstruction image R2) which is a processing result, using the trained model 120B. Specifically, the training function 115 derives the contrast image 670 from the trained model 120B by inputting the non-contrast image 650 and the difference image 660 to the trained model 120B (see step S24).

FIG. 8 is a flowchart showing a reconstruction example of a reconstruction image according to the first embodiment. According to this example, the medical image processing apparatus 1 reconstructs a fourth reconstruction image R4 based on the derived second reconstruction image R2.

(Step S25) Subsequently, the medical image processing apparatus 1 uses the projection function 116 to subsequently project the derived second reconstruction images R2. Specifically, the projection function 116 obtains the estimated projection data EP by performing forward projection of the second reconstruction images R2 derived at step S24.

(Step S26) Subsequently, the medical image processing apparatus 1 uses the integration function 117 to integrate the third projection data P3 serving as a processing target with the estimated projection data EP. Specifically, the integration function 117 obtains the integrated projection data GP by integrating the third projection data P3 that is a processing target acquired in step S21 with the estimated projection data EP obtained in step S25.

(Step S27) Finally, the medical image processing apparatus 1 uses the reconstruction function 113 to reconstruct a reconstruction image based on the integrated projection data GP. Specifically, the reconstruction function 113 reconstructs the fourth reconstruction image R4 corresponding to the second imaging region A2 based on the integrated projection data GP obtained in step S26. After step S27, the medical image processing apparatus 1 terminates a series of operations.

FIG. 9 is a schematic diagram showing a reconstruction example of a reconstruction image according to the first embodiment. According to this example, the medical image processing apparatus 1 reconstructs an enlarged contrast image 900 (an example of the fourth reconstruction image R4) based on the contrast image 670 derived from the trained model 120B.

First, the medical image processing apparatus 1 uses the projection function 116 to perform forward projection of the contrast image 670, thereby obtaining an estimated contrast sinogram 700 (an example of the estimated projection data EP) (see step S25).

The estimated contrast sinogram 700 includes a data region 700A at one end side, a data region 700B at a center side, and a data region 700C at the other end side in a channel direction. The data regions 700A, 700B, and 700C show projection data related to the first imaging region A1. The data region 700B shows projection data related to the second imaging region A2.

Next, the medical image processing apparatus 1 uses the integration function 117 to integrate the contrast sinogram 620 with the estimated contrast sinogram 700, thereby obtaining an integrated contrast sinogram 800 (an example of the integrated contrast data GP) (see step S26).

The contrast sinogram 620 includes a data region 620B at a center side in the channel direction. The data region 620B shows projection data related to the second imaging region A2.

The integrated contrast sinogram 800 includes a data region 800A at one end side, a data region 800B at a center side, and a data region 800C at the other end side in the channel direction. The data regions 800A, 800B, and 800C show projection data related to the first imaging region A1. The data region 800B shows projection data related to the second imaging region A2.

First, the integration function 117 integrates the contrast sinogram 620 with the estimated contrast sinogram 700 so as to make the projection data on the data region 800A close to the projection data on the data region 700A. Second, the integration function 117 integrates the contrast sinogram 620 with the estimated contrast sinogram 700 so as to make the projection data on the data region 800B close to the projection data on the data region 620B. Third, the integration function 117 integrates the contrast sinogram 620 with the estimated contrast sinogram 700 so as to make the projection data on the data region 800C close to the projection data on the data region 700C.

That is, the integrated contrast sinogram 800 may be projection data after the data regions 800A and 800C are replaced with the data regions 700A and 700C, respectively, and the data region 800B is replaced with the data region 620B. Such projection data can also be regarded as "hybrid projection data".

The integration function 117 may apply feathering processing to a boundary between the data regions 800A and 800B or between the data regions 800B and 800C. In the integrated contrast sinogram 800 after the processing, values of the projection data vary smoothly (seamlessly) in the channel direction, thereby improving an image quality of the enlarged contrast image 900 reconstructed from the integrated contrast sinogram 800.

Finally, the medical image processing apparatus 1 uses the reconstruction function 113 to reconstruct the enlarged contrast image 900 corresponding to the second imaging region A2 (i.e., the data region 800B) based on the integrated contrast sinogram 800 (see step S27).

The reconstruction function 113 may reconstruct, based on the integrated contrast sinogram 800, a reconstruction image with a large field of view corresponding to the first imaging region A1 (that is, the data regions 800A, 800B, and 800C). The reconstruction function 113 may apply masking processing to a portion of the reconstruction image, which does not correspond to the second imaging region A2 (that is, the data regions 800A and 800C). The reconstruction image after the processing exhibits a field of view similar to the enlarged contrast image 900.

According to the first embodiment described above, the medical image processing apparatus 1 inputs the contrast sinogram 620 obtained by the contrast scanning of a small field of view related to a heart region of a subject into the trained model 120B, thereby deriving the contrast image 670 with a large field of view including the heart region. At this time, the X-ray CT apparatus 3 only needs to perform contrast scanning exclusively on the heart region of the subject to obtain the contrast sinogram 620, without the need to perform contrast scanning on an imaging region wider than the heart region. Therefore, the medical image processing apparatus 1 can indirectly reduce the exposure dose of the subject.

Furthermore, the medical image processing apparatus 1 obtains the estimated contrast sinogram 700 by performing forward projection of the contrast image 670. The medical image processing apparatus 1 obtains the integrated contrast sinogram 800 by integrating the contrast sinogram 620 with the estimated contrast sinogram 700. The medical image processing apparatus 1 reconstructs the enlarged contrast image 900 of the heart region of the subject based on the integrated contrast sinogram 800.

Herein, the integrated contrast sinogram 800 includes actually measured projection data related to the heart region of the subject, which is derived from the contrast sinogram 620. Therefore, the enlarged contrast-enhanced image 900 is higher in terms of the degree of reproducibility related to the heart region of the subject than the contrast image 670. That is, the medical image processing apparatus 1 can provide a reconstruction image with a higher degree of reproducibility of the heart region of the subject.

In addition, the medical image processing apparatus 1 does not directly reconstruct a reconstruction image from the contrast sinogram 620 truncated in the channel direction. Generally, cupping artifacts, etc., occur in reconstruction images based on truncated projection data. Therefore, the medical image processing apparatus 1 can reduce artifacts by using, for reconstruction, the non-contrast sinogram 610 obtained through non-contrast scanning of a large field of view including the heart region of the subject, as prior information.

Second Embodiment

FIG. 10 is a block diagram showing a configuration example of the X-ray CT apparatus 3 according to a second embodiment. The X-ray CT apparatus 3 includes, as respective modules, a gantry device 30, a bed device 40, and a console device 50. The modules are communicably connected to each other via a bus (BUS) that is a common signal communication path.

The gantry device 30 is a module configured to perform X-ray CT imaging of the subject P. The gantry device 30 includes, as respective components, an X-ray tube 31, a wedge 32, a collimator 33, a high voltage device 34, a detector 35, a DAS 36, a rotating frame 37, and a control device 38. Each component is housed in a housing (not shown) in which a bore 39 is formed.

The X-ray tube 31 is a vacuum tube that irradiates the subject P with X-rays. The X-ray tube 31 generates X-rays by causing thermoelectrons from a cathode filament to collide with an anode target using a high voltage and a filament current supplied from the high voltage device 34. The generated X-rays are irradiated onto the subject P through the wedge 32 and the collimator 33.

The wedge 32 is a filter that adjusts the dose of X-rays irradiated from the X-ray tube 31. The wedge 32 is formed into a concave lens shape that is thin at the center and thick at the periphery, and is made of aluminum, etc. The wedge 32 is switched to a different wedge 32 under control of the control device 38.

The collimator 33 is a window plate that limits an irradiation range of X-rays irradiated from the X-ray tube 31. The collimator 33 includes a slit at its center and is made of lead, etc. The slit of the collimator 33 is adjusted to a given size under control of the control device 38. By the X-rays passing through the slit of the collimator 33, the irradiation range of the X-rays is adjusted to a given size.

The high voltage device 34 is a device that generates a high voltage and a filament current. The high voltage device 34 is of a transformer type or an inverter type. The high voltage device 34 generates a high voltage and a filament current and supplies them to the X-ray tube 31 under control of the control device 38.

The detector 35 is a device that detects X-rays that have passed through a subject P. The detector 35 generates an electrical signal corresponding to the detected X-rays, and transmits the generated electrical signal to the DAS 36. The detector 35 may have a one-dimensional array structure in which a plurality of detection elements are arranged in the channel direction (an X-axis direction; a row direction). Alternatively, the detector 35 may have a two-dimensional array structure in which a plurality of detection elements are arranged in the channel direction and a slice direction (a Z-axis direction; a column direction).

The DAS 36 is a device that generates projection data (sinogram) based on the electrical signal transmitted from the detector 35. In a case where detector 35 is an energy integrating detector (EID), the DAS 36 generates the projection data indicating the dose of X-rays detected by the detector 35. In a case where the detector 35 is a photon counting type detector (PCD), the DAS 36 generates the projection data indicating a count value of X-ray photons detected by the detector 35. The DAS 36 generates projection data by reading electrical signals from the detector 35 under control of the control device 38, and transmits the generated projection data to the console device 50. DAS 36 is an abbreviation for data acquisition system.

The rotation frame 37 is a frame that rotatably supports the X-ray tube 31, the wedge 32, the collimator 33, the high voltage device 34, the detector 35, and the DAS 36 around the rotation axis Z. The rotating frame 37 rotates around the rotation axis Z at a predetermined angular velocity under control of the control device 38.

The control device 38 is a device that controls the wedge 32, the collimator 33, the high voltage device 34, the DAS 36, and the rotating frame 37 under control of the console device 50. The control device 38 includes processing circuitry and a drive mechanism such as a motor, an actuator, etc.

The bed device 40 is a module that moves the subject P in a given axial direction (the X-axis direction, the Y-axis direction, the Z-axis direction). The bed device 40 is installed so as to face a front surface of the gantry device 30. The bed device 40 includes, as respective components, a base 41, a drive mechanism 42, a support frame 43, and a top plate 44.

The base 41 is a structure that supports the drive mechanism 42, the support frame 43, and the top plate 44. The base 41 is installed on a floor surface. The drive mechanism 42 is installed on a top of the base 41. The support frame 43 is installed on a top of the drive mechanism 42. The top plate 44 is installed on a top of the support frame 43.

The drive mechanism 42 is a mechanism that moves the support frame 43 and the top plate 44 in a given axial direction. The drive mechanism 42 moves the support frame 43 and the top plate 44 under control of the control device 38 or the console device 50. The drive mechanism 42 includes a motor such as a direct drive motor, a servo motor, etc.

The support frame 43 is a structure that supports the top plate 44. The support frame 43 is formed of a rigid body such as metal, etc.

The top plate 44 is a flat-shaped structure on which the subject P is placed. The top plate 44 is made of an elastic material such as urethane, etc.

The console device 50 is a module that controls the overall operation of the X-ray CT apparatus 3. The console device 50 includes, as respective components, processing circuitry 51, a memory 52, an input IF 53, a display IF 54, and a communication IF 55. The respective components are communicably connected to each other via a bus that is a common signal communication path.

The processing circuitry 51 is circuitry that controls the overall operation of the console device 50. The processing circuitry 51 has a similar hardware configuration to that of the processing circuitry 11 of the medical image processing apparatus 1. The processing circuitry 51 realizes respective functions (an imaging control function 511, a preprocessing function 512, a reconstruction function 513, a display control function 514, and a system control function 515).

The imaging control function 511 is a function that controls X-ray CT imaging performed by the gantry device 30. For example, the imaging control function 511 controls the X-ray tube 31, the wedge 32, the collimator 33, the high voltage device 34, the detector 35, the DAS 36, and the rotating frame 37 by controlling the control device 38 of the gantry device 30. The imaging control function 511 is an example of an imaging control unit.

First, the imaging control function 511 may obtain the first projection data P1, which is a processing target, by irradiating the first imaging region A1 of the subject P with X-rays while limiting the irradiation range. Second, the imaging control function 511 may obtain the third projection data P3, which is a processing target, by irradiating the second imaging region A2 of the subject P with X-rays while limiting the irradiation range.

The imaging control function 511 may limit an X-ray irradiation range to the first imaging region A1 or the second imaging region A2 by adjusting a size of the slit of the collimator 33. In particular, the imaging control function 511 may limit the X-ray irradiation range to the second imaging region A2 by collimating the X-rays in the channel direction. By collimation, the exposure dose of the subject P can be directly reduced.

First, the imaging control function 511 performs non-contrast scanning for calcium score measurement on an imaging region including the heart region of the subject P. The non-contrast scanning enables the imaging control function 511 to determine a location or range of a field of view. Furthermore, the imaging control function 511 can use the determined position or range of the field of view for subsequent contrast scanning.

Next, the imaging control function 511 performs contrast scanning for time-density curve measurement on a small region based on the heart region of the subject P. As contrast scanning, the imaging control function 511 may perform (1) myocardial perfusion imaging with stress, (2) coronary artery CT angiography without stress, or (3) myocardial delayed contrast imaging.

The preprocessing function 512 is a function that performs various types of preprocessing. For example, the preprocessing function 512 generates corrected projection data by performing preprocessing such as logarithmic transformation, offset correction, sensitivity correction, beam hardening correction, etc., on the projection data transmitted from the DAS 36. The preprocessing function 512 is an example of a preprocessing unit.

The reconstruction function 513 is a function that performs various types of reconstruction. For example, the reconstruction function 513 generates CT image data by performing reconstruction processing such as filtered back projection (FBP), successive approximation reconstruction, etc., on the corrected projection data. The reconstruction function 513 is an example of a reconstruction unit.

The display control function 514 is a function that displays various types of data or information. For example, the display control function 514 displays a CT image based on CT image data on the display IF 54. The display control function 514 is an example of a display control unit.

The system control function 515 is a function that controls various types of operations performed by the processing circuitry 51. For example, the system control function 515 provides an operating system (OS) for the processing circuitry 51 to realize respective functions (the control function 511, a preprocessing function 512, the reconstruction function 513, and the display control function 514). The system control function 515 is an example of a system control unit.

The processing circuitry 51 of the X-ray CT apparatus 3 may realize respective functions similar to those of the processing circuitry 11 of the medical image processing apparatus 1 (the acquisition function 111, the extraction function 112, the reconstruction function 113, the training function 114, the derivation function 115, the projection function 116, the integration function 117, and the system control function 118). That is, the X-ray CT apparatus 3 may execute similar operations to those of the medical image processing apparatus 1.

The memory 52 is a device that stores various types of data or information. The memory 52 has a similar hardware configuration to that of the memory 12 of the medical image processing apparatus 1. For example, the memory 52 stores the projection data, the CT image data, the control program, etc. The memory 52 is an example of a storage unit.

The input IF 53 is an interface that accepts various input operations from a user. The input IF 53 has a similar hardware configuration to that of the input IF 23 of the operation terminal 2. For example, the input IF 53 accepts input operations of collection conditions for projection data, reconstruction conditions for CT image data, etc. The input IF 53 is an example of an input unit.

The display IF 54 is an interface that displays various types of data or information. The display IF 54 has a similar hardware configuration to that of the display IF 24 of the operation terminal 2. For example, the display IF displays a CT image, a graphical user interface (GUI), etc. The display IF 54 is an example of a display unit.

The communication IF 55 is an interface for communicating various types of data or information. For example, the communication IF 55 communicates various types of data or information with the medical image processing apparatus 1, the operation terminal 2, or the medical image storage device 4. The communication IF 55 is an example of a communication unit.

According to the second embodiment described above, the X-ray CT apparatus 3 acquires the first projection data P1 and the third projection data P3, which are processing targets, by adjusting the X-ray irradiation range. Specifically, the X-ray CT apparatus 3 limits the X-ray irradiation range in the contrast scanning to the second imaging region A2. Therefore, the X-ray CT apparatus 3 can reduce the dose of exposure of the subject P as compared to a case in which the first imaging region A1 is irradiated with X-rays.

According to at least one of the embodiments described above, the dose of exposure can be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising processing circuitry configured to:

acquire first projection data obtained by performing non-contrast scanning on a first imaging region of a subject, and second projection data obtained by performing contrast scanning on the first imaging region;

extract third projection data corresponding to a second imaging region in the first imaging region from the second projection data;

reconstruct a first reconstruction image based on the first projection data, a second reconstruction image based on the second projection data, and a third reconstruction image based on a difference between the first projection data and the third projection data; and derive the second reconstruction image as a processing result from the first projection data and the third projection data as processing targets, using a model trained with training data in which the first reconstruction image and the third reconstruction image are set to input data and the second reconstruction image is set to correct answer data.

2. The medical image processing apparatus according to claim 1, wherein the processing circuitry is configured to:

obtain estimated projection data by performing forward projection of the derived second reconstruction image;

obtain integrated projection data by integrating the third projection data as the processing target with the estimated projection data; and reconstruct a fourth reconstruction image corresponding to the second imaging region based on the integrated projection data.

3. The medical image processing apparatus according to claim 1, wherein the processing circuitry is configured to train the model using the training data.

4. A medical image processing method comprising:

acquiring first projection data obtained by performing non-contrast scanning on a first imaging region of a subject, and second projection data obtained by performing contrast scanning on the first imaging region;

extracting third projection data corresponding to a second imaging region in the first imaging region from the second projection data;

reconstructing a first reconstruction image based on the first projection data, a second reconstruction image based on the second projection data, and a third reconstruction image based on a difference between the first projection data and the third projection data; and deriving the second reconstruction image as a processing result from the first projection data and the third projection data as processing targets, using a model trained with training data in which the first reconstruction image and the third reconstruction image are set to input data and the second reconstruction image is set to correct answer data.

5. An X-ray CT apparatus comprising processing circuitry configured to:

acquire first projection data obtained by performing non-contrast scanning on a first imaging region of a subject, and second projection data obtained by performing contrast scanning on the first imaging region;

extract third projection data corresponding to a second imaging region in the first imaging region from the second projection data;

reconstruct a first reconstruction image based on the first projection data, a second reconstruction image based on the second projection data, and a third reconstruction image based on a difference between the first projection data and the third projection data; and derive the second reconstruction image as a processing result from the first projection data and the third projection data as processing targets, using a model trained with training data in which the first reconstruction image and the third reconstruction image are set to input data and the second reconstruction image is set to correct answer data.

6. The X-ray CT apparatus according to claim 5, further comprising:

an X-ray tube configured to irradiate the subject with X-rays;

a collimator configured to limit an irradiation range of X-rays irradiated from the X-ray tube;

a detector configured to detect, as an electrical signal, X-rays which have been irradiated from the X-ray tube through the collimator and have passed through the subject; and a data acquisition system configured to generate projection data based on the electrical signal, wherein the processing circuitry is configured to:

control the X-ray tube, the collimator, the detector, and the data acquisition system; and obtain the first projection data as the processing target by irradiating the first imaging region of the subject with X-rays while limiting the irradiation range, and obtain the third projection data as the processing target by irradiating the second imaging region of the subject with X-rays while limiting the irradiation range.

* * * * *